United States Patent [19]
Bakhoum

[11] Patent Number: 5,179,497
[45] Date of Patent: Jan. 12, 1993

[54] GROUND-FREE STATIC CHARGE REMOVAL DEVICE

[76] Inventor: Ezzat G. Bakhoum, 613 Clarion Dr., Durham, N.C. 27705

[21] Appl. No.: 707,691

[22] Filed: May 30, 1991

Related U.S. Application Data

[63] Continuation-in-part of Ser. No. 691,350, Apr. 25, 1991, abandoned.

[51] Int. Cl.[5] ............................................. H05F 3/00
[52] U.S. Cl. ........................................ 361/212; 307/9.1; 361/217; 361/220
[58] Field of Search ............... 361/212, 220, 232, 217, 361/218; 307/9.1, 10.1

[56] References Cited
U.S. PATENT DOCUMENTS

| | | | |
|---|---|---|---|
| 3,634,726 | 1/1972 | Jay | 361/220 |
| 4,048,667 | 9/1977 | Brennecke | 361/213 |
| 4,107,755 | 8/1978 | Kiefer | 361/220 |
| 4,156,267 | 5/1979 | Spaulding et al. | 361/230 |
| 4,181,698 | 12/1979 | Carpenter | 361/212 |
| 4,186,421 | 1/1980 | Twitchett | 361/220 |
| 4,271,451 | 6/1981 | Metz | 361/213 |
| 4,333,123 | 6/1982 | Moulden | 361/213 |
| 4,333,124 | 6/1982 | Tamura et al. | 361/214 |
| 4,498,116 | 2/1985 | Saurenman | 361/213 |
| 4,523,252 | 6/1985 | Wallen | 361/212 |
| 4,605,984 | 8/1986 | Fielder | 361/220 |
| 4,638,398 | 1/1987 | Brennecke et al. | 361/214 |
| 4,639,825 | 1/1987 | Breidegan | 361/212 |
| 4,766,903 | 8/1988 | Esper | 361/232 |
| 4,849,851 | 7/1989 | Cubbison, Jr. | 361/212 |
| 4,862,315 | 8/1989 | Cubbison, Jr. | 361/212 |
| 5,004,425 | 4/1991 | Hee | 361/212 |

OTHER PUBLICATIONS

Pulse, Digital and Switching Wave Forms, Millmen & Taub, McGraw-Hill, 1984, pp. 613-617.

*Primary Examiner*—Jeffrey A. Gaffin

[57] ABSTRACT

A ground-free device for removing static charges from semi-conductive or conductive bodies. The device includes a storage capacitor, a conductive contact connected to the storage capacitor, and an air capacitor connected to the storage capacitor, in which a voltage below the breakdown voltage of the air is imposed on the air capacitor, e.g., by an RC-controlled transistor oscillator circuit. The device provides high efficiency removal of static charge, e.g., from the metallic bodies of cars and aircraft.

30 Claims, 4 Drawing Sheets

GROUND-FREE STATIC CHARGE REMOVAL DEVICE

CROSS-REFERENCE TO RELATED APPLICATION

This is a continuation-in-part of U.S. application Ser. No. 07/691,350 filed Apr. 25, 1991 in the name of Ezzat G. Bakhoum for "Corporeal Static Charge Removable Device" now abandoned.

BACKGROUND OF THE INVENTION

1. Field of the Invention

This invention relates to a ground-free device for removing static electrical charge from a conductive or semi-conductive body, and particularly a device of such type which may be
 worn on the human body in a compact form; or
 mounted on transportation vehicles, such as cars and aircrafts, for removal of static charges therefrom.

2. Description of the Related Art

While the present invention is broadly useful for removing static electrical charge from conductive and semi-conductive charged bodies, two specific applications are in particular concern:

The first application is the discharge of static electricity from the human body. Historically, a number of means and methods have been developed for "grounding" the human body to dissipate static electricity therefrom. Typically, these approaches have utilized wire connections for attaching the body to a large metallic object (or true ground), to utilize the surplus of positive/negative charges in the metallic object to neutralize the body. These approaches, while effective to preclude the build-up of static charge in the bodies of individuals, suffer from the disadvantage that mobility thereby is severely circumscribed, as well as dexterity which in many instances is required to perform functions or tasks desired of the "grounded" individual.

The second application is related to transportation vehicles (cars and aircrafts). It is known that static electricity build-up during the movement of these vehicles is responsible for pains, fatigue, and drowsiness of passengers, as well as damage of electronic equipment in the vehicle. Historically, chains and conductive rods, attached to the bodies of these vehicles, have been used to drain static charges by means of friction with the surrounding medium (air or asphalt). These approaches, apart from being ineffective, suffer from the great disadvantage that friction produce sparks, and eventually can result in a fire, especially in the case of automobiles.

Apart from corporeal, or transportation-related applications, a number of systems have been devised in the art to preclude static electricity build-up.

U.S. Pat. No. 3,634,726 issued Jan. 11, 1972 to Pierre Jay describes an apparatus for removing static electricity from plastic films. The apparatus requires a ground connection.

U.S. Pat. No. 4,523,252 issued Jun. 11, 1985 to J. O. Wallen describes a device for eliminating static electricity on machines and charged materials. The device depends on the operation of a tunnel diode, and must be connected between charging media and the machine part.

U.S. Pat. No. 4,180,698 issued Dec. 25, 1979 to R. B. Carpenter describes a system for protection of objects located on the surface of the earth from the effects of atmospherics.

U.S. Pat. No. 4,766,903 issued Aug. 30, 1988 to Herbert Esper describes a device for detecting and removing static charges from the human body. The device, however, requires a ground connection.

U.S. Pat. No. 4,849,851 issued Jul. 18, 1989 to R. J. Cubbison, Jr. describes a static electric discharge device which may be contained in a wrist-mountable unit. The device uses a high electric field to ionize the air molecules. The Cubbison, Jr. patent suffers various deficiencies in use, and will not achieve its intended purpose of effectively removing charges from the body, mainly for the following two reasons:

1. It is claimed that the electric field of the body can separate the closely-spaced positive and negative ions of the air. In fact, the electric field at any particular point on the skin is negligibly small, because the charge is distributed all over the body (that is why a high electric field is used to ionize the air in the first place). For that reason, the claimed effect is very slow in nature.

2. From an electric-circuit view point, a more significant deficiency is apparent. This deficiency is simply the use of a DC voltage from a power supply. It is clear that whether the air is near or at the breakdown point, a small current will flow in the circuit because the circuit is "closed". This by no means will result in the withdrawal of charges from the body, since, in this case, the ions of the air are themselves the current carries. In summary: "Static charges cannot flow into a closed electrical circuit".

Accordingly, it would be a significant advance in the art to provide a ground-free device for removing static electrical charge from the human body and from other conductive or semi-conductive bodies, which is characterized by a high static charge removal efficiency, e.g., levels of at least 95%, in a small fraction of a second. This is the object of the present invention.

SUMMARY OF THE INVENTION

In one aspect, the present invention relates broadly to a ground-free device for removing static electrical charge from conductive and semi-conductive bodies (such as the human body), comprising:

a storage capacitor comprising first and second terminals;

a conductive body contact means for establishing electrical contact with the body, and connected to the storage capacitor at a first terminal thereof;

an air capacitor having first and second terminals, one of which is connected to the second terminal of the storage capacitor; and means for imposing on the air capacitor a voltage which is sufficient for effecting ionization of the air therein but is below the breakdown voltage of the air; and for keeping the circuit electrically open at the terminals of the air capacitor. This means suitably includes a large-delay, impulse-type oscillator, and a high voltage capacitor.

In a further aspect, the ground-free device described above is encased in a unitary housing having openings or otherwise configured to allow air circulation therethrough.

In a specific preferred embodiment, suitable for application to transportation vehicles such as cars, trucks, buses, aircrafts, etc., the device of the present invention as broadly described hereinabove may be further enhanced by the provision of an isolation transformer at the output terminals of an impulse-type oscillator including a transformer generating high voltage, or other power source for the circuitry including the storage capacitor, conductive body contact means, air capacitor, and means for imposing a voltage on the air capacitor and keeping an electrically open circuit at the terminals of the air capacitor. This modification accommodates the typical situation in which the body of the vehicle is connected to a negative (ground) terminal of a battery or other power supply means.

Other aspects and features of the invention will be more fully apparent from the ensuing disclosure and appended claims.

DETAILED DESCRIPTION OF THE INVENTION, AND PREFERRED EMBODIMENTS THEREOF

The present invention is based on the fundamental concept that a conductive or semi-conductive body, and particularly the human body, can be discharged by touching one side (i.e., plate or terminal) of a capacitor, and that such capacitor may be relatively small in size.

In most situations where friction occurs during bodily movements, the body is charged positively because the human body is more conductive than most other materials (clothing, upholstery, carpet, etc.). This is also true when the body is traveling in a car, because the tires are charged positively, and the positive charge flows to the body of the car and to the bodies of passengers. The present invention is therefore concerned with the removal of positive charges from the human body, and from transportation vehicles.

The potential on the human body, in many cases, can reach substantially elevated potential levels, e.g., on the order of 30,000 volts. Despite this high potential, the charge of the body is very small. This is because the capacitance between the body and the ground (or large metallic object) is small. This capacitance, generally, does not exceed 1 nF ($10^{-9}$ Farads).

The voltage (V), the charge (Q) and the capacitance (C) are related by the following equation:

$$Q = CV$$

For a potential of 30,000 volts on the body, and a capacitance of 1 nF, the charge is $$Q = 10^{-9} \times 3000 = 3 \times 10^{-5} \text{ Coulombs.}$$

To appreciate the magnitude of this charge, viz., as being a very small value, a capacitor holding the same charge, at a potential of 6 volts, would have a capacitance of $$C = \frac{Q}{V} = \frac{3 \times 10^{-5}}{6} = 5 \times 10^{-6} \text{ Farads} = 5\mu F.$$

which is a relatively small capacitor.

Figure 1:
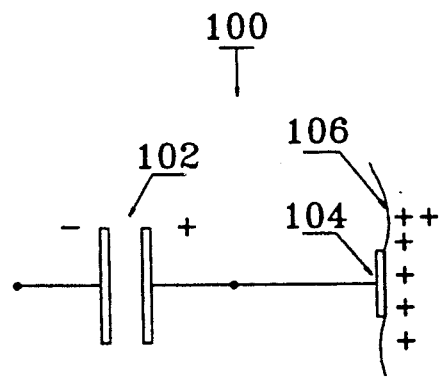
FIG.1. is a schematic representation illustrating the general principle of capacitive removal of charges from a conductive or semi-conductive body, as employed in the present invention.

FIG. 1 illustrates the basic concept underlying the present invention. This figure shows a static charge removal device 100 comprising a capacitor 102 which is connected to a body contact member 104. The body contact member in turn is in skin contact with the body 106. (It is to be noted that the charge on transportation vehicles is of the same order of magnitude as that of the human body, because the charge on any metallic object always resides on the surface, not inside the conductor. The potential on the body of a car, with respect to ground, generally does not exceed 100,000 volts after long trips).

Experiments showed that 50%-60% of the total charge on the human body will be dragged into the capacitor instantaneously (the same results were verified for conductive bodies). This is a result of the regenerative induction inside the capacitor: few positive charges from the body create an electric field which ionizes some of the air molecules and attracts several electrons to the negative electrode of the capacitor (as mentioned earlier, this effect is negligibly small at the beginning). Now, by opposite induction, many more positive charges are collected at the positive electrode. The process is self-amplified rapidly, and the air is positively charged. (In this respect, it is to be noted that even in the absence of such capacitive device, when the human body is wet, charges from the body will flow directly into the air, as for example on hot summer days when the body is actively perspiring. In this situation, the skin becomes conductive, and charges flow from inside the body to the surface of the skin). It should be noted that the regenerative induction only happens because the capacitor remains unbalanced all the time (which is not the case when the capacitor is charged with a battery or power source).

The role of the regenerative induction is seen by understanding that the static charge is initially distributed all over the body. At any particular point on the skin, the field is negligibly small. As the induction process multiplies the charges on both sides of the capacitor, the positive electric field grows and ionizes an increasing number of air molecules. It is worth mentioning, however, that induction does not allow the voltage on the capacitor to grow unlimited. As the rate of flow of charges from the body decreases, the process slows, and finally stops when the body becomes neutral. (It was mentioned earlier that the potential on the body can reach 30,000 volts. This does not happen until all the charge is condensed at one point on the skin; i.e., when the body approaches a large metallic object. Regenerative induction takes place in this case also).

The 50%-60% efficiency obtained experimentally is due to the fact that the air (a poor conductor), cannot supply a sufficient number of electrons as the positive field grows. (The human body can be modeled as a large dielectric medium having a resistance of 1-2 MΩ ($10^6$ Ohms). In theory, capacitors in RC networks charge/discharge exponentially over time. The remaining charge on the body will take an infinite time to flow to the capacitor; however, the exact mathematics of this theory do not apply here).

In the FIG. 1 system, the capacitor can be initially uncharged, or charged to a small voltage. Experiments showed that the initial charge on the capacitor will contribute no effect in accelerating/retarding the induction process, especially when a large capacitor is used.

Figure 2:
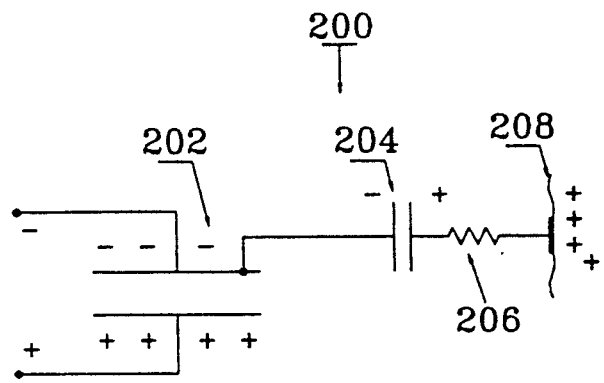
FIG. 2. is a schematic representation of a basic circuit for removal of charges with an efficiency of at least 95%, according to the present invention.

The relatively low efficiency achieved by the FIG. 1 system is overcome by the static charge removal device of FIG. 2. The purpose of the device shown in FIG. 2 is to achieve an efficiency of 95%-100% in neutralizing the body instantaneously. In this device 200, a conductive body contact element, similar to element 104 of FIG. 1, is disposed in contact with body 208, such body having positive charge thereon. The body contact element is joined by suitable wire or other electrically conductive means to the storage capacitor 204, with resistor 206 disposed therebetween. Capacitor 204 functions as a storage capacitor for static charges withdrawn from the body. (The capacitance of storage capacitor 204 is suitably at least 5 μF, and more preferably is at least 200 μF, with a voltage rating of at least 6 V. For transportation vehicles, the capacitance of capacitor 204 is preferably at least 1500 μF, with a voltage rating of at least 16 V). The resistor 206 is an optional component of the device whose purpose is to protect the human body from electric shock, if the body is initially charged before touching the device. (A suitable range of values for resistor 206 is 100K-1 MΩ). The negative electrode of the storage capacitor 204 is connected to an air capacitor 202 inside which a large electric field exists, thereby providing a large number of ionized air molecules. A D.C. voltage (not shown) is applied to the air capacitor, which is large enough to ionize many air molecules, but not to cause breakdown of the air (the breakdown electric field for the air is 3000 volts/mm. The air capacitor 202 may for example have an air gap of 0.5 millimeters, so that the use of a potential of 1000 V will maintain the air well below the breakdown point). The D.C. voltage must be maintained by a third, large capacitor (not shown in FIG. 2) arranged in parallel with capacitor 202, not by a power supply (as will be discussed later) to keep the circuit electrically open.

Under the influence of the large positive field inside the storage capacitor 204, electrons are easily collected from the highly ionized air inside the capacitor 202, and the storage capacitor is charged. The device 200 thereby effectively "pumps" the charge from the body into the air. Ideally, the air capacitor 202 should be as large as possible (when the application is considered for the human body, a suitable range of capacitances for a parallel-plate air capacitor will range from 5 pF ($5 \times 10^{-12}$ Farads) to 30 pF, with a 0.5 mm air gap. These capacitance values permit the air capacitor to be effectively utilized in a relatively compact device. For transportation vehicles, the air capacitor is preferably at least 100 pF). Moreover, the air capacitor 202 may be constructed in a cylindrical shape, or other arbitrary shapes and configurations, and possibly having a fixed or alternatively adjustable air gap.

Figure 3:
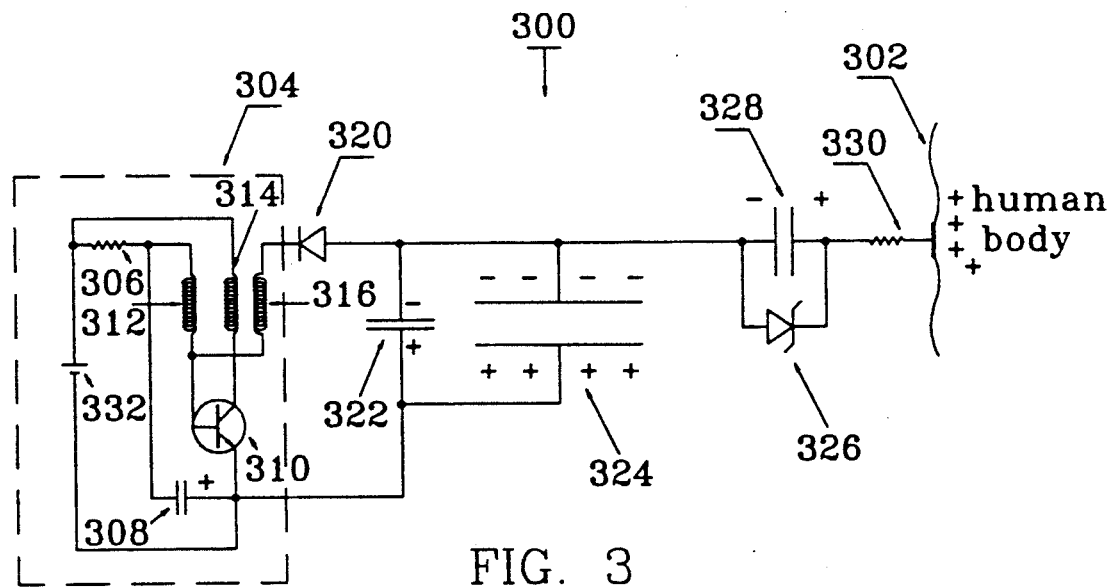
FIG. 3. is a schematic representation of a complete device for removal of static charges from the human body, according to the present invention.

FIG. 3 is a schematic representation of a complete device 300 for removal of static charges from a human body 302. The device 300 has associated therewith a circuit 304 for generating high voltage. The circuit 304 is of a known type (an astable transistor blocking oscillator), being described more fully in *Pulse, digital and switching waveforms*, by Millman and Taub, McGraw Hill, 1984, pages 613-617. The oscillator is RC-controlled by resistor 306 (having a selected value of, but not limited to, 3.3 MΩ), and capacitor 308 (having a selected value of, but not limited to, 22 μF). The oscillator circuit comprises a transistor 310 and a transformer including coils 312, 314, and 316, the latter coil providing a terminal of the transformer which is joined to rectifying diode 320, as shown. (The voltage rating of diode 320 is suitably at least 1000 V). The transformer of circuit 304 is of a type conventionally employed in electronicflash cameras, e.g., having a turns ratio of 100. Circuit 304 includes a power source 332, which may for example comprise a 12 V battery.

Connected to rectifying diode 320, and in parallel with air capacitor 324, is a capacitor 322 for storing the voltage generated by circuit 304, which appears as impulses at the terminal of the transformer connected to the rectifying diode 320. (The capacitance of capacitor 322 is suitably at least 0.1 μF, and the voltage rating is suitably at least 1000 V). Capacitor 322 is needed because the duration between successive impulses, adjusted by the RC combination of the oscillator, is about 15 seconds, and the air capacitor 324 (of only few pico-Farads of capacitance) cannot hold the charge for such a long period. It is very important to note that once capacitor 322 is charged, the circuit is electrically open between successive impulses (i.e., for a duration of 15 seconds) because the diode 320 is reverse biased. By this technique, the ions of the air will not contribute to any external current flow. This will allow electrons to be collected by the storage capacitor 328 (as in the previously described system of FIG. 2). It is therefore to be appreciated that the high voltage generating circuit must be impulse-type, and must provide a large period of time between successive impulses (the 15-second period of oscillation was selected because the capacitor 322 was found to lose about 10% of its charge during this period. Ideally, the period of oscillation should be as large as possible, because the device will not function under a power-supplied DC voltage).

An optional resistor 330 is disposed between the storage capacitor 328 and the body-contacting element as a shock-preventative aspect of the device 300.

Connected in parallel to the storage capacitor 328 is a Zener diode 326. The purpose of the Zener diode is to prevent the voltage on the storage capacitor from growing beyond the nominal voltage. The Zener diode is an optionally added feature, which may be deleted from the device 300 if the capacitance of the storage capacitor 328 is sufficiently large so that the voltage thereon does not exceed the nominal voltage. In this respect, the capacitance of the storage capacitor 328 is preferably at least 200 μF, and the voltage rating is preferably at least 6 V. The rating of the Zener diode is suitably 5 V.

It should be noted that the device 300 can operate without the storage capacitor 328, however, the process of charge dissipation will be slow. The role of the regenerative induction inside capacitor 328 is to make the process instantaneous. As a further aspect of performance, it should be noted that the device works best if the point of contact with the skin is wet.

While the devices of FIGS. 1, 2, and 3 have been illustratively described hereinabove with reference to specific voltage, resistance, and capacitance values, it will be recognized that the device may be variously configured, utilizing other parametric values of voltage, resistance, and capacitance, etc., within the skill of the art.

Figure 4:
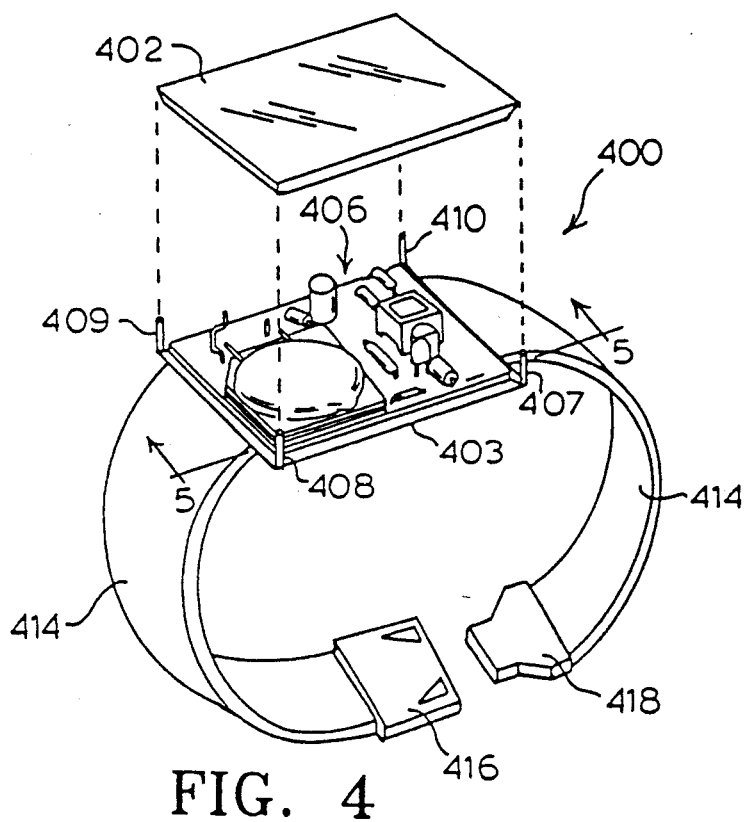
FIG. 4. is a perspective, partially exploded view of a wrist-mountable static charge removal device according to one embodiment of the invention.
Figure 5:
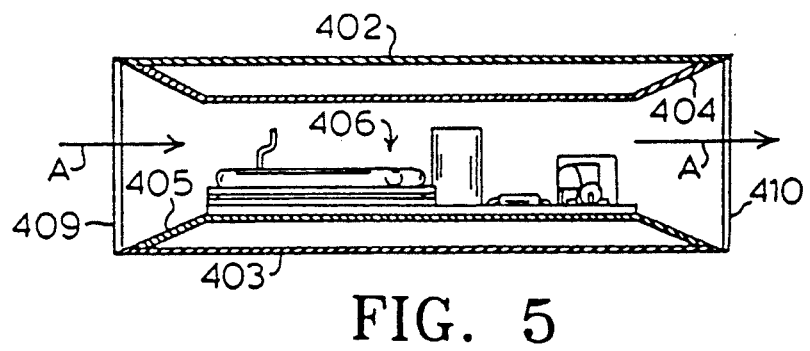
FIG. 5. is a cross-sectional elevation view, taken along line 5—5 of FIG. 4, showing the details of the device of FIG. 4.

FIG. 4 is a perspective view of a wrist-mountable device in accordance with the present invention, as shown in partially exploded view, with FIG. 5 showing a sectional, elevational view of the device along line 5—5 of FIG. 4. As shown, the wrist-mountable device 400 includes a circuit board assembly 406, comprising the storage capacitor, air capacitor and related components. The circuit board assembly is mounted on a frusto-pyramidal support 405, which is in turn joined to a lower conductive base plate 403 having vertical support members 407, 408, 409, and 410. The vertical support members are joined to a top enclosure member, comprising a frusto-pyramidal member 404 and an upper base plate 402. The body-contact terminal of resistor 330 is electrically coupled to the lower base plate 403. This unitary enclosure is joined to respective wrist strap segments 414, having free ends featuring clasp elements 416 and 418, whereby the device 400 may be mounted on and secured to the wrist of a wearer. In this manner, movements of the arm of the wearer will result in forced convective flow of air through the device to thereby "sweep out" the air to which charge has been dissipated from the body of the wearer of the device, e.g., in the direction indicated by arrows A in FIG. 5.

Figure 6:
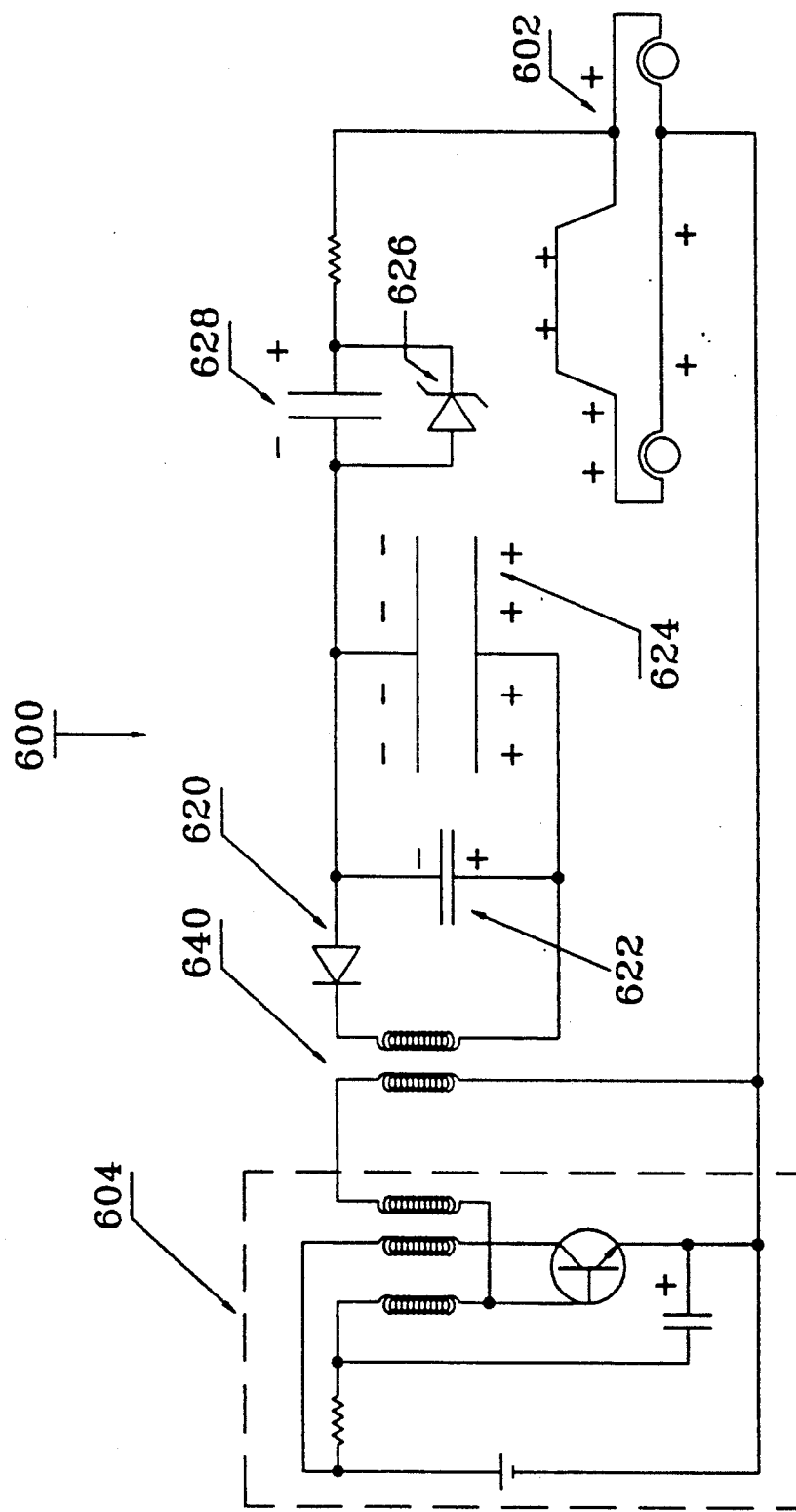
FIG. 6. is a schematic representation of a complete device for removal of static charges from a conductive body, such as the body of a vehicle, according to the present invention.

When the application is considered for transportation vehicles, it should be noted that the body of the vehicle is usually connected to the negative (ground) terminal of the battery (as shown in FIG. 6). This situation will require a further modification to the basic circuit 300, since, in this case, the connection of the high voltage terminal to the body of the vehicle 602 will effectively result in the application of a short-circuit over the air capacitor. The modification can simply be the insertion of an isolation transformer at the output terminals, before the rectifying diode 320. The isolation transformer is shown as the component 640 in the modified circuit 600 of FIG. 6. (Alternatively, the circuit can be fed from an independent power source, or a combination of oscillator/isolation transformer/rectifier, driven from the main power source).

The circuit assembly of the device shown in FIG. 6 includes an oscillator circuit 604, a rectifying diode 620, and a capacitor 622 in parallel with air capacitor 604, analogous to the arrangement of circuit 300 discussed hereinabove in connection with FIG. 3 hereof.

Figure 7:
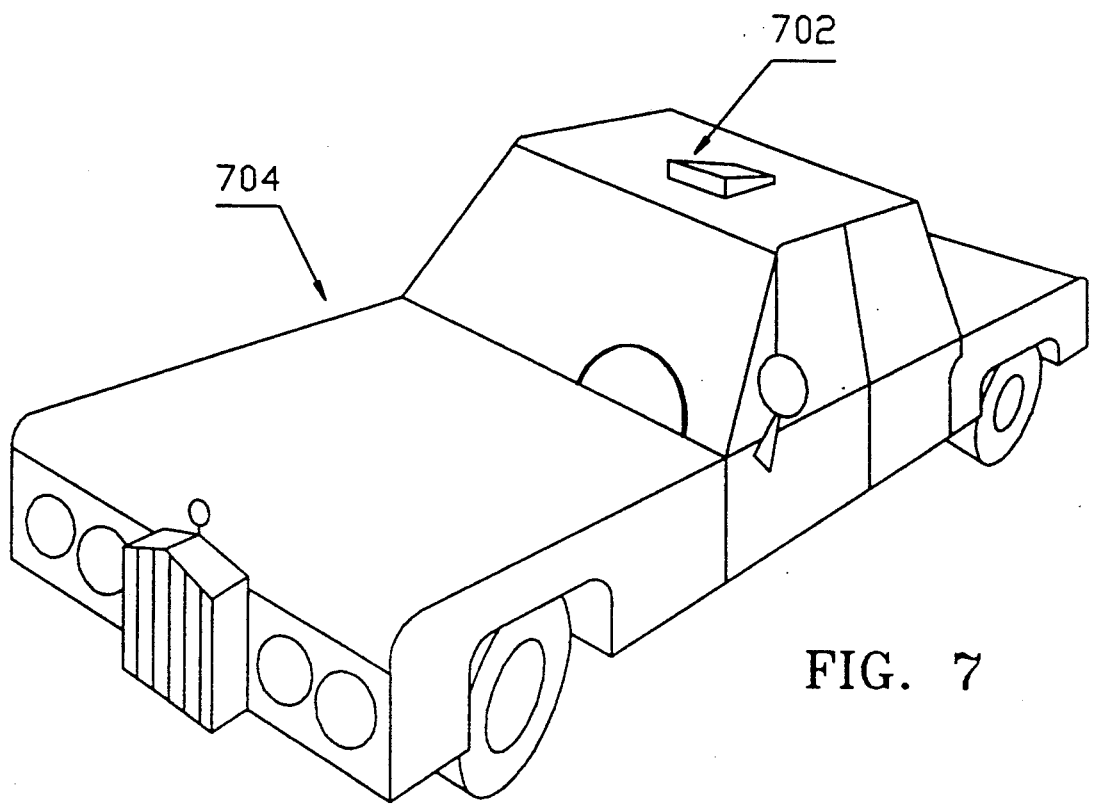
FIG. 7. is a perspective view of a vehicle-mountable static charge removal device according to one embodiment of the invention.

In the device 600, the storage capacitor 628 is preferably at least 1500 μF, with a voltage rating of at least 16 V. The capacitance of air capacitor 624 is at least 100 pF (based on a 0.5 mm air gap). The rating of Zener diode 626 is suitably 15 V. Further, it should be noted that it is preferable to mount the air capacitor outside the body of the vehicle to allow air circulation therethrough. Such an arrangement is shown in FIG. 7, where an air capacitor 702 is mounted outside the body of a vehicle 704, such vehicle being a ground-vehicle or an aircraft.

Figure 8:
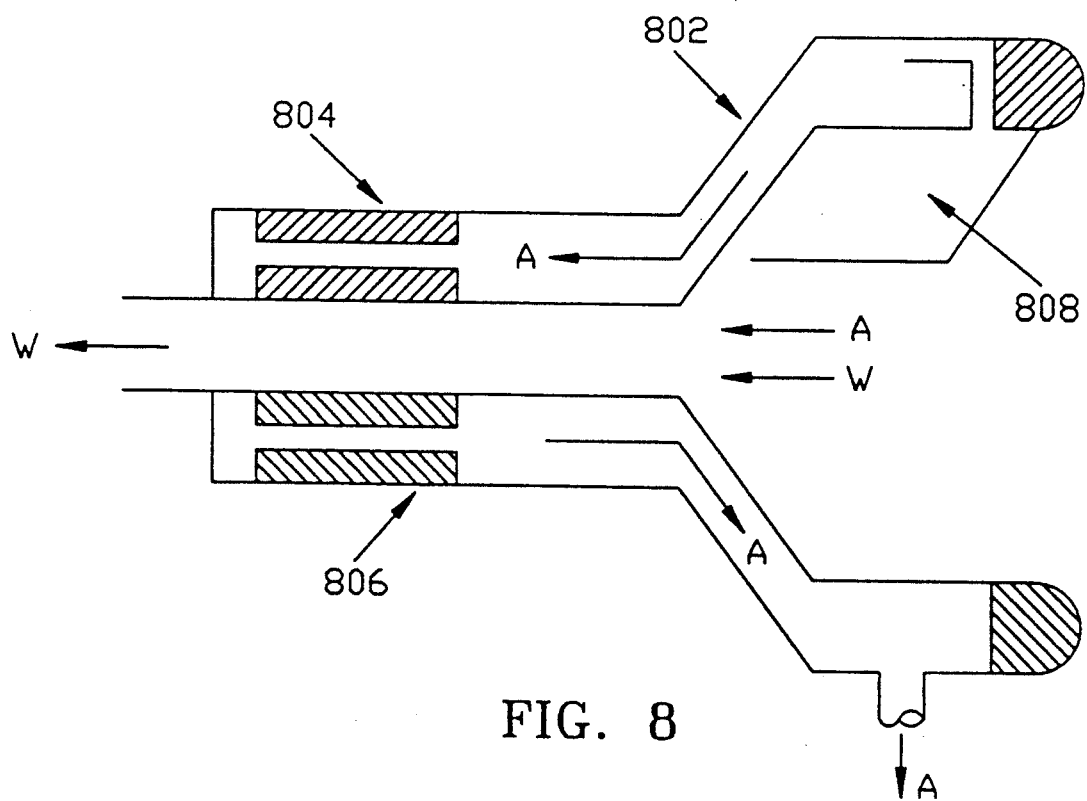
FIG. 8. is a sectional view of a plastic housing for the air capacitor, designed to permit circulation of air, but not rain drops, therethrough.

Another point of interest, when the invention is applied to transportation vehicles, is that only air should be allowed inside the air capacitor, but not water or rain drops. Since the resistance of a drop of water ranges from 50 to 100 KΩ, this resistance will overload the circuit and may damage the transistor. FIG. 8 shows a sectional view of a possible plastic housing 802 for two air capacitors, 804 and 806, which could be connected in parallel. The housing is designed to allow air circulation through the capacitors, but not rain drops. In the housing shown in FIG. 8, water is separated from air because of the sudden pressure drop in chamber 808. Inside the housing, the directions of flow of the air-water mixture and of dry air are shown by the arrows labeled W and A, respectively.

It will be apparent from the foregoing that the static removal device of the present invention is a ground-free device which requires no connections or couplings to true ground or to large metallic charge-dissipation structures. Further, it will be recognized that the device of the invention may be compactly configured in any of various conformations so as to be body-mountable in character.

The device of the invention achieves a high degree of removal of charges from conductive and semi-conductive bodies (and in particular, the human body), substantially instantaneously, and at a high efficiency, e.g., on the order of 95% to 100%.

The device of the invention employs an arrangement comprising two capacitors, one (the storage capacitor) providing a large capacitance for storing the charge extracted from the body, and the other (the air capacitor) providing a large electric field for generating opposite charges, whereby charge is flowed from the storage capacitor to the air capacitor and dissipated into the air at the locus of the air capacitor.

The storage capacitor may be of any suitable conventional type, as for example electrolytic, tantalum, ceramic, etc., but preferably electrolytic. The air capacitor, as mentioned, may have a fixed or adjustable air gap, and may have different physical configurations, as for example parallel-plate, cylindrical, etc., with single or multi-layers.

A large D.C. voltage is imposed on the air capacitor, which must be maintained by a third, large capacitor, to keep the circuit electrically open between successive high voltage impulses which are generated by an impulse-type, large-delay oscillator circuit. For high efficiency, the delay is preferably at least 2 seconds.

A large resistance may be placed between the storage capacitor and the contact of the device with the human skin. This resistance is preferred, but is not necessary to the charge-removal function of the device. When the application is considered for transportation vehicles, the resistance is also preferred, in case humans come in contact with the body of the vehicle.

A Zener diode may be placed across the storage capacitor, to keep the voltage on that capacitor below the nominal voltage. This Zener diode could be eliminated, or replaced by a large resistor, with the disadvantage of possibly exceeding the nominal voltage on the storage capacitor during prolonged charging situations.

While the invention has been described hereinabove with reference to removing positive charges from the body, it will be recognized that the terminals of the capacitors may be reversed to allow the device to withdraw negative charges as well.

In addition, while the invention has been shown in two particular embodiments as a wrist-mountable structure for the human body, and as a roof-mountable structure for automobiles, it will be appreciated that the device may be configured in any suitable manner, to be mountable on or coupleable with any other part of the body, to effect the removal of static charges therefrom.

Finally, while no particular discharge method has been described for the storage capacitor, it should be noted that such capacitors lose the charge gradually over long periods of time, by internal dissipation. This is adequate in practice, since transportation vehicles usually stop for several hours after long trips. Moreover, it should be noted that such long trips will result in a charge build-up that gives rise to only few volts on the storage capacitor. Nevertheless, an appropriate discharge circuit could be devised by those skilled in the art without departing from the scope of the invention.

Accordingly, while the invention has been described with reference to specific aspects, features, and embodiments, it will be appreciated that various modifications, alternatives, and other embodiments are possible within the broad scope of the invention, and the invention therefore is intended to encompass all such modifications, alternatives, and other embodiments, within its scope.

What is claimed is:

1. A ground-free device for removing static electrical charge from a conductive or semi-conductive body, comprising:
    a storage capacitor comprising first and second terminals;
    a conductive body contact means for establishing electrical contact with the body, and connected to the storage capacitor at a first terminal thereof;
    an air capacitor having first and second terminals, one of which is connected to the second terminal of the storage capacitor; and
    means for imposing on the air capacitor a voltage which is sufficient for effecting ionization of the air therein but is below the breakdown voltage of the air, and for keeping the circuit electrically open at the terminals of the air capacitor.

2. A device according to claim 1, wherein the means for imposing a voltage on the air capacitor and keeping an electrical open circuit the terminals of the air capacitor, comprises a large-delay, impulse-type oscillator; a diode; and a high voltage capacitor arrangement in parallel with the air capacitor.

3. A device according to claim 2, wherein the voltage rating of the diode is at least 400 V.

4. A device according to claim 2, wherein the voltage rating of the diode is at least 1000 V.

5. A device according to claim 2, wherein the capacitor of the high voltage capacitor is at least 0.1 $\mu$F.

6. a device according to claim 2, wherein the voltage rating of the high voltage capacitor is at least 400 V.

7. a device according to claim 2, wherein the voltage rating of the high voltage capacitor is at least 1000 V.

8. A device according to claim 2, wherein the delay between successive impulses is at least 2 seconds.

9. A device according to claim 2, wherein the impulse-type oscillator comprises a transformer that generates high voltage.

10. A device according to claim 2, wherein the impulse-type oscillator comprises and RC-controlled transistor circuit.

11. A device according to claim 2, wherein the impulse-type oscillator comprises a battery.

12. A device according to claim 1, further comprising a resistor connected between the conductive body contact means and the storage capacitor, having sufficient resistance to protect the body, when charged, from electric shock upon initial contact of the body with the conductive body contact means of the device.

13. A device according to claim 12, wherein the resistance of the resistor is in the range of 100 K$\Omega$ to 1 M$\Omega$.

14. A device according to claim 1, wherein the capacitor of the storage capacitor is in the range of 5 $\mu$F to 200 $\mu$F.

15. A device according to claim 1, wherein the voltage rating of the storage capacitor is at least 6 V.

16. A device according to claim 1, wherein the air gap of the air capacitor is at least 0.3 mm.

17. A device according to claim 1, wherein the air gap of the air capacitor is at least 0.5 mm.

18. A device according to claim 1, wherein the air capacitor has a capacitance in the range of 5 pF to 30 pF.

19. A device according to claim 1, wherein the storage capacitor, air capacitor, and means for imposing a voltage on the air capacitor and keeping an electrical open circuit at the terminals of the air capacitor, are disposed in a unitary housing configured to allow air circulation therethrough.

20. A device according to claim 1, further comprising means to limit voltage on the storage capacitor to voltage values below the nominal voltage.

21. A device according to claim 20, wherein the voltage-limiting means comprise a Zener diode in parallel with the storage capacitor.

22. A device according to claim 1, constructed and arranged for mounting on the human body.

23. A device according to claim 1, configured as a wrist-mountable unit.

24. A ground-free device for removing static electrical charge from transportation vehicles, comprising:
    a storage capacitor comprising first and second terminals;
    a conductive body contact means for establishing electrical contact with the body, and connected to the storage capacitor at a first terminal thereof;
    an air capacitor having first and second terminals, one of which is connected to the second terminal of the storage capacitor; and
    means for imposing on the air capacitor a voltage which is sufficient for effecting ionization of the air therein but is below the breakdown voltage of the air, and for keeping the circuit electrically open at the terminals of the air capacitor.

25. A device according to claim 24, wherein the capacitance of the storage capacitor in the range of 1000 $\mu$F to 3000 $\mu$F.

26. A device according to claim 24, wherein the voltage rating of the storage capacitor is in the range of 10 V to 16 V.

27. A device according to claim 24, wherein the capacitance of the air capacitor is at least 100 pF.

28. A device according to claim 24, further comprising an isolation transformer at the output terminals of the high voltage transformer.

29. A ground-free device for removing static electrical charge from a conductive or semi-conductive body, consisting essentially of:
    an electrical charge storage capacitor comprising first and second terminals, wherein the second terminal is constructed and arranged for direct exposure to an ambient air environment; and a conductive body contact means for establishing electrical contact with the body and connected to the storage capacitor at the first terminal thereof;

whereby charge flowing from the conductive or semi-conductive body through the conductive body contact means to the electrical charge storage capacitor is dissipated to air of the ambient air environment at the second terminal of the storage capacitor.

30. A device according to claim 29, wherein conductive or semi-conductive body comprises a human body.

* * * * *